United States Patent [19]

Bourbon et al.

[11] Patent Number: 5,458,889

[45] Date of Patent: Oct. 17, 1995

[54] METHODS AND COMPOSITIONS FOR INHIBITING OR DESTROYING VIRUSES OR RETROVIRUSES

[75] Inventors: Pierre Bourbon, Toulouse, France; Pierre Lagny, Kildare, Ireland; Pierre Billot, Neuilly sur seine, France

[73] Assignee: Atlantic Pharmaceutical Products Limited, Kildare, Ireland

[21] Appl. No.: 20,176

[22] Filed: Feb. 22, 1993

Related U.S. Application Data

[63] Continuation of Ser. No. 509,997, Apr. 16, 1990, abandoned, which is a continuation-in-part of Ser. No. 53,374, May 22, 1987, Pat. No. 4,917,901.

[30] Foreign Application Priority Data

May 22, 1986 [FR] France .................................. 86 07310
Dec. 8, 1986 [EP] European Pat. Off. .............. 86402716

[51] Int. Cl.⁶ .................................................... A61K 31/14
[52] U.S. Cl. ............................ 424/673; 424/52; 424/675; 424/676; 435/235.1; 435/236; 435/237; 435/238; 514/642; 514/868; 514/931
[58] Field of Search ..................................... 514/642, 931, 514/868; 424/52, 673, 675, 676; 435/235.1, 236, 237, 238, 5

[56] References Cited

U.S. PATENT DOCUMENTS

| | | | |
|---|---|---|---|
| 4,006,218 | 2/1977 | Sipos | 424/54 |
| 4,471,054 | 9/1984 | Lattore et al. | 435/238 |
| 4,490,353 | 12/1984 | Crawford et al. | 424/52 |

FOREIGN PATENT DOCUMENTS 54-107519  2/1978  Japan ...................... 514/642

*Primary Examiner*—Shailendra Kumar
*Attorney, Agent, or Firm*—Curtis, Morris & Safford

[57] ABSTRACT

This invention relates to a method and composition for inhibiting or destroying viruses or retroviruses in a mammalian host. The method comprises contacting the viruses or retroviruses with a composition. The composition comprises an active ingredient capable of inhibiting or destroying viruses or retroviruses, for example, a surfactant, and an activating ingredient capable of inhibiting or destroying one or more enzymes associated with viruses or retroviruses, for example, a fluorinated compound capable of releasing fluoride anions, and an excipient.

10 Claims, No Drawings

METHODS AND COMPOSITIONS FOR INHIBITING OR DESTROYING VIRUSES OR RETROVIRUSES

This application is a continuation of application Ser. No. 07/509,997, filed Apr. 16, 1990, abandoned, which in turn is a continuation in part of prior U.S. application Ser. No. 07/053,374 filed May 22, 1987, now U.S. Pat. No. 4,917,901, the disclosure of which application is expressly incorporated herein by reference.

BACKGROUND OF THE INVENTION

The invention relates to the inhibition or destruction of unicellular living creatures such as protozoa, microbes, bacteria, gametes, fungi or others, and viruses. Consequently, it aims in particular at the technical fields of local contraception, of antibiotherapy, antisepsis, as part of either pharmacy or cosmetic and of disinfection.

Hereafter, the term "inhibition" of a unicellular living creature or of a virus means either hindering its proliferation, or making it incapable of accomplishing some functions that it usually accomplishes. The term "destroying" means killing the unicellular living creatures or viruses.

With regard to the invention, the term "substance" hereafter means any chemical compound or association of chemical compounds having at least one given function or one function common to the compounds, and which can be included in the composition of a finished product, generally associated with one or more excipients and possibly with other substances. Similarly, the term "product" means a usable finished product. Thus, a finished product is generally constituted of at least one excipient and of several substances, each substance being constituted of one or several chemical compounds having similar or identical functions. The term "substance" may correspond to an actual fact, but may be purely theoretical and functional in the case of intricate mixtures where the compounds have multiple effects or which effects interfere with each other. The functional classification in compounds, substances, products does not necessarily correspond to the process of manufacture of the product and to the mixture actually obtained in the practice. As usual, the term "composition" is used here and in all the following text to design a pharmaceutical or cosmetic substance.

DESCRIPTION OF THE PRIOR ART

Substances inhibiting or destroying unicellular living creatures, either in the biological, pharmaceutical, cosmetic fields, or even in broader fields such as disinfection or others, are already known.

In particular, spermicidal compositions are known from U.S. Pat. Nos. 4,339,441 and 4,359,475.

Numerous chemical compounds usable in local contraception methods for living beings are also known. In particular, it is known that surfactants lowering the interfacial tension (e.g. quaternary ammoniums, nonoxynols, derivatives of amidoethylglycinate on fatty acids, methyltauride sodium oxysalt . . . ) and some other compounds such as phenylmercuric nitrate, para-menthanylphenylpolyoxethylene ether or trisodium salt of polysaccharide sulphuric ether, have inhibiting or destroying effects on unicellular living creatures, in particular have spermicidal effects.

Substances mechanically acting on the spermatozoa, for example by immobilizing them, are also known. U.S. Pat. No. 4,368,186 describes such effects, and more particularly the association of "poloxamer" with spermatozoa inhibiting agents, in view of controlling gelation and solubilization of the products and thus mechanically increasing the efficiency of the inhibiting agents with an additive or a synergistic effect.

Locally contraceptive compositions are also known, particularly spermicidal ones, including such chemical compounds and which are locally usable for inhibiting the fertilization ability of gametes, particularly of spermatozoa of human or animal beings.

These known compositions include a concentration of inhibiting chemical compound superior to the minimal inhibiting concentration, called MIC, in solution or suspended in a pharmaceutically acceptable excipient which depends on the galenical form used. It is known that in order to have all the spermatozoa which are contained in 0.2 milliliters of sperm killed in less than 5 seconds (conditions of the total spermicidal test according to the standards of IPPF, International Planned Parenthood Federation), the concentration of the spermicidal active ingredient in 1 milliliter of pharmaceutical composition must be superior or equal to the minimal inhibiting concentration, called MIC, of this active ingredient. The MIC of a chemical compound depends on this compound, but also on the conditions in which it is used, i.e. on the galenical form including the composition.

More generally, pharmaceutical or cosmetic compositions including at least one basic active ingredient inhibiting or destroying at least one unicellular living creature and drugs or cosmetic products including such compositions are known.

In the field of antisepsis and disinfection, numerous active ingredients are known: halogens (chlorinated or iodinated derivatives . . . ), aldehydes, alcohols, phenols, acids, metals (silver, copper, mercury, zinc salts . . . ), amidines, biguanides, diphenylurea, oxydants (hydrogen peroxide, potassium permanganate . . . ), colouring agents, agents lowering the interfacial tension and wetting agents (cationic, anionic, amphoteric or organic).

Antiseptic and/or disinfectant and/or antiprotozoal and/or antifungal and/or antibiotic and/or antiviral products including such inhibiting or destroying substances, and manufacturing processes of these substances or compositions, are also known.

The known substances or compositions are generally satisfactory but set some problems for their practical use.

These problems are essentially the following:

First of all, it is generally desirable to obtain a total inhibition or destruction efficiency of the unicellular living creature(s) or of the viruse(s), i.e. an inhibition or destruction rate of 100% in the practical application circumstances. Well, this is not always the case when no strict precautions for use are taken, or when a limitation of the doses of active ingredient are required (for example in the case of the cosmetic).

Moreover, it is generally desirable to exhibit an activity against one or more given unicellular living creatures or viruses, e.g. gametes or pathogens, without giving rise to short-term and/or long-term undesirable side effects (activity against other unicellular living creatures, irritations, damages to the environment . . . ). But, in the practice, it has been found that the doses required for solving the first above mentioned problem give rise to long-term side effects (generally linked to regular use), and even to short-term side effects (use by fits and starts). In the medical field, some teratogen and/or cancerigen effects have been noted from certain threshold doses and with certain active ingredients. In the field of disinfection, some undesirable effects may be noted against the materials to be disinfected.

OBJECTS OF THE INVENTION

An object of the invention is the increasing of the inhibiting or destroying ability of a substance or composition including a given limited concentration of basic inhibiting or destroying active ingredient, without increasing this concentration. Yet another object of the invention is the reduction of the concentrations of the basic active ingredients without decreasing the inhibiting or destroying ability of the substance or composition for all that and in order to avoid the side effects and to better control the selectivity towards the various unicellular living creatures and viruses.

In particular, the invention aims at furnishing a new pharmaceutical or cosmetic composition, more particularly locally contraceptive and a drug or product including such a composition, which may be used either by fits and starts, or regularly and continuously at long-term, without risking side effects such as teratogen or cancerigen, and which efficiency is total, i.e. which percentage of failures is statistically null or insignificant, and this within the regular mere circumstances of use (with no particular precautions).

Moreover, the invention aims at furnishing a locally contraceptive pharmaceutical product, easy to use and totally efficient, i.e. which gives some results similar to those of the oral contraception without having the drawbacks thereof.

The invention also aims at providing a chemical compound usable in a local contraception method.

Finally, another objective of the invention is the reduction of the doses of the active ingredients inhibiting or destroying unicellular living creatures or viruses in the drugs, cosmetic products, or disinfectant products, especially in the antiseptic, antibiotic, bactericidal, antiprotozoal, antifungal, spermicidal, antiviral . . . products.

SUMMARY OF THE INVENTION

The invention relates to a substance inhibiting or destroying at least one unicellular living creature or virus in particular such as protozoan, microbe, bacterium, gamete, fungus or other, characterized in that it comprises at least one basic active ingredient inhibiting or destroying said unicellular living creature or virus, and at least one ingredient inhibiting or destroying at least one enzyme associated to said living creature or virus, said latter ingredient being an activator —preferably having a synergistic effect— of said former basic active ingredient.

Preferably, the ingredient inhibiting or destroying at least one associated enzyme, called hereafter "activating ingredient" "activator" is an agent hindering the working of the couple enzyme/substrate.

But it has been surprisingly found that such an agent could advantageously be formed with fluoride anion F$^-$ emitted from a fluorinated compound, either spontaneously, or after enzymic action. It has also been found that, in some cases, the basic active ingredient itself is capable of emitting an activating ingredient, and/or that the activating ingredient itself is an active ingredient inhibiting or destroying at least one unicellular living creature or virus.

More precisely, it has been noted that such a fluorinated compound has by itself an ability for inhibiting or destroying unicellular living creatures and viruses, and that such a fluorinated compound has a synergistic effect with the associated basic active ingredient(s).

A feature of the invention is to provide a local contraceptive composition, more particularly spermicidal composition, characterized in that it comprises at least one chemical compound capable of emitting fluoride anion F$^-$, as an active ingredient inhibiting or destroying gametes, directly or by potentiation, and an excipient.

The invention also provides a drug, an antiseptic and/or disinfectant —more particularly locally antiseptic—, and/or antiprotozoal —more particularly locally antiprotozoal—, and/or bactericide —more particularly locally bactericide—, and/or antifungal —more particularly locally antifungal—, and/or antibiotic —more particularly locally antibiotic—, and/or antiviral product, a cosmetic product —more particularly local cosmetic such as a synthetic soap or milk— and a contraceptive product which is locally applied in contact with gametes —more particularly ovule, cream, gel, solution, foam, tablet, soluble waffle, tampon, vaginal suppository— characterized in that they comprise a substance or a composition according to the invention.

Here and hereafter, the term "local" and its derivatives means that the product is used at a predetermined place to be treated, e.g. the vagina or other anatomic parts, so that the effect is produced in the environment near this place, against unicellular living creatures or viruses that come into contact with the product, and this in opposition to general administrations (e.g. oral administration or parenteral administration).

A substance, a composition, a drug, a product, a chemical compound according to the invention are as well directed to local administrations as to general administrations. For example, a spermicide according to the invention may be locally applied. Besides, when wishing to overcome the resistance effects of the pathogenic unicellular living creatures against the regular therapies, one would rather use general administrations of the invention.

The invention is also concerned with the use in a cosmetic product of a composition including at least one basic active ingredient and at least one fluorinated chemical compound capable of emitting fluoride anion F$^-$ as active ingredient of said basic active ingredient(s); with the use of a fluorinated chemical compound capable of emitting fluoride anion F$^-$ for manufacturing a substance including at least one basic active ingredient, as activor of said basic active ingredient; with the use of a substance or a composition according to the invention in the manufacture of a drug to be used as antibiotic and/or antiprotozoal and/or bactericide and/or antifungal and/or antiseptic and/or antiviral; and with the use of a substance or a composition according to the invention in the manufacture of a local contraceptive for human or animal being, in particular inhibiting or destroying gametes. The invention also provides a manufacturing process of a substance or composition according to the invention inhibiting or destroying at least one unicellular living creature —in particular such as protozoan, microbe, bacteria, gamete, fungus or other, virus—, characterized in that at least one basic active ingredient inhibiting or destroying said unicellular living creature or virus is mixed with at least one ingredient inhibiting or destroying an enzymetic system associated to said living creature or virus, said latter ingredient being an activator of said former basic active ingredient.

The invention also provides a chemical compound including ionizable fluorine for use in a local contraception method for living beings, more particularly in a locally contraceptive product for human or animal beings according to the invention or in a substance or a composition according to the invention.

According to the invention an activating ingredient inhibiting or destroying at least one enzyme associated to said unicellular living creature or virus induces a remarkable sensibilization of said unicellular living creature or virus to egressions from outside, in particular to the action of said basic active ingredient inhibiting or destroying said unicellular living creature or virus, by "blocking" the couple enzyme/substrate. It is effectively known that each unicellular living creature or virus owns a vital enzymetic system. Besides, unicellular living creatures or viruses may emit, upon some circumstances (e.g. resistance to antibiotic), some particular enzymes providing the destruction of some aggressing agent (e.g. lactamase destroying penicillins), these enzymes being called "protecting enzymes". The invention lies in inhibiting the function of these enzymes, and thus fragilizing the unicellular living creature by creating the optimal conditions for the efficiency of the active ingredients against it. This brings numerous advantages compared to the prior art, which are on one hand to satisfy the aims above mentioned and, on the other hand, to be able to act in a selective manner upon a given unicellular living creature or upon a given family of unicellular living creatures by acting upon a given enzyme or upon a given family of enzymes. In the case of viruses, the invention aims to inhibiting the enzymes that are necessary for their formation and/or their replication. Hereafter "associated enzymes" means vital and/or protecting enzymes of unicellular living creatures and/or viruses.

The inventors have determined that fluorine in the ionized state $F^-$ has a particularly efficient and benefic effect as activating ingredient against the associated enzymes, and this under trifling regular concentrations. Moreover, ionized fluorine $F^-$ is very common, economical and relatively easy to use. Its manipulations and utilizations are well controlled, as well as the side effects that he may provide according to the doses used.

The invention provides a process of inhibition or destruction of at least one unicellular living creature or virus —in particular such as protozoan, microbe, bacterium, gametee, fungus or other—, characterized by the use of at least one basic active ingredient inhibiting or destroying said unicellular living creature and at least one ingredient inhibiting or destroying at least one enzyme associated to said living creature or virus, said latter ingredient being an activator —preferably having a synergistic effect— of said former active ingredient; and such a process including the use of at least one substance or composiiton according to the invention.

DETAILED DESCRIPTION OF THE INVENTION

The invention relates to the inhibition or destruction of unicellular living creatures such as protozoa, microbes, bacteria, gametes, fungi, whether pathogenic or not, and viruses. The invention has mostly two different kinds of uses: either uses in the cosmetic or pharmaceutical field (case of the following examples of spermicides or bactericides acting against pathogenic agents), or uses in more common fields such as agriculture, disinfection (following example) or others. In all the cases, a substance according to the invention is characterized in that it includes at least one basic active ingredient inhibiting or destroying said unicellular living creature or virus, and at least one ingredient inhibiting or destroying at least one enzyme associated to said living creature or virus, said latter ingredient thus being an activator —preferably having a synergetic effect when being itself capable of inhibiting or destroying said living being or virus— of said former basic active ingredient.

The function of the activating ingredient consists in annihilating the working of the enzymatic system associated to said living creature(s) or virus(es). In this way, the inventors have found that such activating ingredient is advantageously an agent hindering the working of the couple enzymesubstrate, preferably anion fluoride $F^-$ emitted from a fluorinated compound, e.g. a metallic derivative of fluorine. Some very good results have been noted with sodium fluoride, calcium fluoride, potassium fluoride, aluminium fluoride, tin fluoride, ammonium fluoride, or sodium monofluorophosphate or other. For example, the following unicellular living creatures or viruses may be concerned with the invention:

gametes (spermatozoa, ovula)
gram-positive cocci such as staphylococci and streptococci
gram-negative cocci such as gonococci
gram-positive bacilli
gram-negative bacilli such as colibacilli or *Escherichia coli*
acid-alcoholo-fast bacilli such as mycobacteria, e.g. *Mycobacterium smegmatis*
spiral bacteria such as spirochetes, e.g. treponema
miscellaneous bacteria such as chlamydia
flagellate protozoa, such as trichomonas
miscellaneous yeasts such as *Candida albicans*
viruses or retroviruses, such as (Human Immunodeficiency Virus) and Herpes.

For example: the following enzymes associated to at least one such unicellular living creature or virus may be concerned with the invention (Table 1):

TABLE 1

| ENZYME | SUBSTRATE |
| --- | --- |
| Alkaline Phosphatase | 2- naphthyl phosphate |
| Esterase (C 4) | 2- naphthyl butyrate |
| Esterase Lipase (C 8) | 2- naphthyl caprylate |
| Lipase (C 14) | 2- naphthyl myristate |
| Leucine arylamidase | L- leucyl -2- naphthylamide |
| Valine arylamidase | L- valyl -2- naphthylamide |
| Cystine arylamidase | L- cystyl -2- naphthylamide |
| Trypsin | N- benzoyl -DL- arginine -2- naphthylamide |
| α Chymotrypsine | N- glutaryl-phenylalanine- 2- naphthylamide |
| Acid phosphatase | 2- naphthyl phosphate |
| Naphthol-AS-B1- phosphohydrolase | Naphthol-AS-B1- phosphate |
| α galactosidase | 6-Br-2- naphthyl α D- galactopyranoside |
| β galactosidase | 2- naphthyl -βD- galactopyranoside |
| β glucuronidase | naphthol-AS-B1-βD-glucuronide |
| α glucosidase | 2- naphthyl-αD- glucopyranoside |
| β glucosidase | 6-Br-2- naphthyl-βD- glucopyranoside |
| N- acetyl -β glucosaminidase | 1- naphthyl-N-acetyl-βD- glucosamimnide |
| α mannosidase | 6-Br-2- naphthyl-αD- mannopyranoside |
| α fucosidase | 2- naphthyl-αL-fucopyranoside |

A basic active ingredient used in a substance or composition according to the invention is for example a cationic or anionic or amphoteric or non-ionic surfactant lowering the interfacial tension, preferably a quaternary ammonium. Benzalkonium chloride or other alkylbenzalkonium is an example of cationic surfactant. A methyltauride sodium oxysalt is an example of anionic surfactant. A derivative of amidoethylglycinate on fatty acids is an example of amphoteric surfactant. A nonoxynol is an example of non-ionic surfactant. The basic active ingredient may also advantageously be phenylmercuric nitrate or para-menthanylphenylpolyoxyethylene ether or a trisodium salt of polysaccharide sulfuric ether or other (halogen, aldehyde, alcohol, phenol, acid, metal, amidine, biguanide, diphenylurea, oxydant, colouring agent . . . ).

In the various tested uses, it has been shown that the alone activating ingredient alone has generally by itself also an activity directly against said unicellular living creature or virus. It has then surprisingly been noted that the association of the activating ingredient with the basic active ingredient has a synergistic effect in so far as the results obtained are not only corresponding to the sum of the results expected from the only presence of the basic active ingredient and of the activating ingredient, but, on the contrary, are superior to this sum.

The efficiency of such active ingredients or activators can be measured with the minimal inhibiting concentration called MIC which corresponds to the concentration of the active ingredient inducing the inhibition or the death of the whole unicellular living creatures or viruses in a given time.

Advantageously, in a substance according to the invention, the anion fluoride $F^-$ concentration emitted by the activating fluorinated compound is inferior to the minimal inhibiting concentration (MIC) of fluoride anion $F^-$ without basic active ingredient.

Similarly, the basic active ingredient concentration in a substance according to the invention can be inferior to the minimal inhibiting concentration (MIC) of this basic active ingredient without activating ingredient. Even so and surprisingly, such a substance, according to the invention, has a total efficiency, i.e. at least equal to the one of substances including either only fluoride anion $F^-$ in a concentration superior or equal to its MIC. or only a basic active ingredient in a concentration superior or equal to its MIC.

Besides, the basic active ingredient itself may also be capable of emitting an activating ingredient, such as fluoride anion $F^-$. A substance or a composition according to the invention may include several basic active ingredients which functions may be identical or various and/or several activating ingredients acting on at least one enzyme associated to one or several of the basic active ingredients.

A substance or a composition according to the invention can be used in multiple ways for obtaining products, and according to the way of using the products, can be used in local or general administration.

Among the particularly advantageous uses of products according to the invention, the various therapeutical possible uses as drug can be mentioned. As a matter of fact, the problem of inhibition or destruction of unicellular living creatures or viruses is encountered in an always increasing number of therapeutical uses. This may be either the fight against some pathogenic agents, and then the products are antibiotic and/or antiprotozoal and/or bactericide and/or antifungal and/or antiseptic and/or antiviral, or even against some non-pathogenic agents such as gametes, e.g. spermatozoa within the framework of contraception, in particular local contraception.

A substance or a composition according to the invention can also advantageously be used in a cosmetic product with such doses and concentrations that do not permit its classification as a pharmaceutical product.

As a matter of fact, for example, the efficient concentrations of fluorinated chemical compounds and even of basic active ingredients can be lowered in such an extent that they become inferior to the threshold values separating the pharmaceutical and cosmetic fields, and this without lowering the efficiency of the product by this way.

A substance or a composition according to the invention can also be used in products which are neither cosmetics nor pharmaceutical products, for example as antifungal, antiprotozoal, antiseptic, antibiotic or other in the field of agriculture, or also in the field of the disinfection of surfaces.

PREFERRED EMBODIMENTS OF THE INVENTION

The preferred embodiment of the invention presently known is the one of the products locally used on the genitals of male and/or female mammals, as spermicides and/or bactericides for fighting against sexually transmissible diseases (STD).

Benzalkonium chloride and nonoxynol are preferably used as active ingredient. Any metallic derivative of fluorine, e.g. sodium fluoride is preferably used as activating ingredient. All the known galenical forms are usable, such as preferably ovule, cream, gel, solution, foam, tablet, soluble waffle, tampon, vaginal suppository or others.

The proportions to be used of active and activating ingredients depends on the galenical form since only the actual concentrations induced in vivo are important as regards to the efficiency of the product.

These proportions must vary between the MIC and the maximal concentrations from which side effects are induced. In local administration, intolerances (irritations) of the treated parts must be avoided. In general administration, toxic concentrations must be avoided.

Thus, the Benzalkonium Chloride concentration in vivo is preferably 1.2% (in weight) and the fluoride anion $F^-$ concentration in vivo is preferably 0.5% (in weight).

Several preferred embodiments of the invention are hereafter described, in several tested uses, by referring to tests carried out on several unicellular living creatures.

I) USE OF THE INVENTION FOR LOCAL CONTRACEPTION:

The invention advantageously provides a spermicidal pharmaceutical product locally applied so that it comes into contact with sperm and kills or inhibits the spermatozoa.

A spermicidal pharmaceutical product according to the invention may be presented under various galenical forms: tablet, ovule, soluble, cream, gel, soluble waffle, tampon, foam, vaginal suppository, inserted within the vagina before sexual intercourse for preventing a fertilization by killing or inhibiting the spermatozoa before they come into contact with the ovula.

A product according to the invention comprises a composition which includes at least one chemical compound according to the invention which includes ionizable fluorine, i.e. capable of emitting fluoride anion $F^-$, as an active ingredient spermicidal directly or by potentiation.

A chemical compound according to the invention is capable of emitting fluoride anion $F^-$ when soluted, in particular in aqueous solution. For example, it is constituted of a metallic derivative of fluorine such as sodium fluoride, calcium fluoride, potassium fluoride, aluminium fluoride, tin fluoride, ammonium fluoride, sodium monofluorophosphate . . . , or an organic fluorinated compound such as a fluorinated amine.

For example, for measuring the spermicide activity of a chemical compound, one may use the total spermicidal test according to the standards of IPPF, which consists in finding the minimal inhibiting concentration called MIC (expressed with a weight percentage) of the chemical compound in one milliliter of solution inducing the death of all the spermatozoa which are contained in 0.2 milliliter of sperm in less than 5 seconds. The test is carried out on at least 6 sperms from various donors, satisfying the following minimal conditions from IPPF:

age of the sample: two hours;
density per $mm^3$: 50 million spermatozoa;
mobility: 50% of the spermatozoa should move forward
  fastly when examined at 35°–37° C. in a recent sample;
viscosity: ejaculum conveniently liquefied, not filaceous and
  homogeneous-looking with the naked eye;
collected in sterile glass tubes hermetically closed, preserved at 37° C.

The inventors have found that, under these conditions, fluoride anion $F^-$ has a spermicide activity of 100% according to the IPPF test when present at a titer of 5 ppm (e.g. 5 milligrams per liter).

A pharmaceutical spermicidal composition according to a first variant of the invention includes at least one fluorinated chemical compound capable of emitting fluoride anion $F^-$ as unique active inhibiting or destroying ingredient. The titer of $F^-$ in the composition is advantageously superior to 4.5 ppm, preferably about 5 ppm when a 100% inhibiting composition is desired.

Moreover, the inventors have found that fluoride anion $^-$, in addition to this direct spermicide activity, has a spermicide activity by potentiation of known spermicidal compounds. Therefore, a composition according to the invention is advantageously constituted on one hand of at least one basic active spermicidal ingredient such as a cationic, or anionic, or amphoteric or non-ionic surfactant lowering the interfacial tension, or even para-menthanylphenylpolyoxyethylene ether or a trisodium salt of polysaccharide sulfuric ether or other, on second hand of at least one fluorinated compound according to the invention capable of emitting fluoride anion $F^-$, and finally of a pharmaceutical excipient and various common additives (anti-oxydant, . . . ).

In a composition according to the invention, the basic active ingredient concentration may be inferior to the MIC of this basic active ingredient without ion $F^-$, the composition being nevertheless 100% inhibiting, i.e. satisfying the total spermicidal test of IPPF. A composition according to the invention may include an admixture of several basic active ingredients inhibiting gametes and/or an admixture of several various fluorinated chemical compound.

Hereafter, the percentages are given in weight.

The preferred embodiments of the invention for its uses in local contraception are as follows:

OVULES:

| | |
|---|---|
| benzalkonium chloride | 1.20% |
| anion $F^-$ | 0.50% |
| (e.g. sodium fluoride) | |

Excipients: semi-synthetic glycerides or cacao butter, or gelatin or glycerin and purified water, antioxygens, antiseptics.

CREAMS AND MILKS:

| | |
|---|---|
| benzalkonium chloride | 1.20% |
| anion $F^-$ | 0.50% |
| (e.g. sodium fluoride) | |

Excipients: distilled or purified water, humectants, emulsifiers, stabilizers, antioxygens, antiseptics (to be included in variable proportions according to the viscosity and pH to be obtained).

OINTMENTS AND POMMADES:

| | |
|---|---|
| benzalkonium chloride | 1.20% |
| anion $F^-$ | 0.50% |
| (e.g. sodium fluoride) | |

Excipients: distilled or purified water, emulsifier, excipients of the kind of the fatty compounds (vaseline, lanoleine, lanovaseline, stearovaseline), stabilizers, antioxygens, antiseptics (to be included in variable proportions according to the viscosity and pH to be obtained).

GEL:

| | |
|---|---|
| benzalkonium chloride | 1.20% |
| anion $F^-$ | 0.50% |
| (e.g. sodium fluoride) | |

Excipients: soluble derivatives of cellulose compatible with the cationic surfactants, distilled or purified water, glycerin, sorbitol, antioxygens, antiseptics (to be included in variable proportions according to the viscosity and pH to be obtained).

SOLUBLE WAFFLE:

| | |
|---|---|
| benzalkonium chloride | 1.20% |
| Anion $F^-$ | 0.50% |
| (e.g. sodium fluoride) | |

Excipients: polyvinyl alcohol, glycerin, sorbitol, propylene glycol, distilled or purified water, antioxygens.

TABLETS:

| | |
|---|---|
| benzalkonium chloride | 25 mg per tablet |
| anion $F^-$ | 10 mg per tablet |
| (e.g. sodium fluoride) | |

Excipients: lactose, magnesium stearate, cellulose, amylum, citric acid, sodium bicarbonate.

SYNTHETIC SOAPS:

| | |
|---|---|
| benzalkonium chloride | 2% |
| anion $F^-$ | 1% |
| (e.g. sodium fluoride) | |

Excipients: foaming and wetting products compatible with quaternary ammonia (e.g. amphoteric surfactant such as betaine or amino-betaine) emollients, stabilizers, antioxygens, antiseptics.

SOLUTIONS:

| | |
|---|---|
| benzalkonium chloride | 0.50% |
| anion $F^-$ | 0.25% |
| (e.g. sodium fluoride) | |

Excipients: distilled or purified water, ethanol, antioxygens, glycerin, sorbitol, antiseptics (to be included in variable proportions according to the pH to be obtained).

COMPARATIVE TEST N· 1

The MIC of various known spermicidal compounds were determined with the IPPF test. The following results have been obtained by 1 milliliter of composition reacting with 0.2 milliliter of sperm and by determining the minimal concentration of the spermicidal compounds that induces the death of all the spermatozoa in 5 seconds, and this with 6 sperms from various donors.

| Spermicidal compound | MIC (% in weight) |
|---|---|
| p-menthanylphenylpolyoxyethylene ether | 0.006 |
| Trisodium salt of polysaccharide sulfuric ether | 0.007 |

-continued

| Spermicidal compound | MIC (% in weight) |
|---|---|
| Anionic surfactant (methyltauride sodium oxysalt) | 1 |
| Cationic surfactant (benzalkonium chloride) | 0.006 |
| Non-ionic surfactant (nonoxynol 9) | 0.006 |
| Amphoteric surfactant (derivative of amidoethylglycinate on fatty acids) | 0.001 |

TEST N· 2

The same total spermicidal test of IPPF was carried out with 1 milliliter of composition already containing 0.0001% (in weight) of fluoride anion $F^-$ reacting upon 0.2 milliliter of sperm, by determining the minimal concentration of the spermicidal compounds that induces the death of all the spermatozoa in 5 seconds, and this with 6 sperms from various donors.

| Spermicidal compound | MIC (% in weight) |
|---|---|
| p-menthanylphenylpolyoxyethylene ether | 0.003 |
| Trisodium salt of polysaccharide sulfuric ether | 0.0025 |
| Anionic surfactant (methyltauride sodium oxysalt) | 0.50 |
| Cationic surfactant (benzalkonium chloride) | 0.002 |
| Non-ionic surfactant (nonoxynol 9) | 0.003 |
| Amphoteric surfactant (derivative of amidoethylglycinate on fatty acids) | 0.0005 |

It is thus noticeable that the inhibiting ability of the known spermicidal ingredients is much improved with the adjunction of ionizable fluorine in the composition. A composition according to the invention may therefore contain very little basic active spermicidal ingredient, in particular in a concentration inferior to the minimal inhibiting concentration of this active ingredient without ion $F^-$.

Moreover, the concentration of ion $F^-$ associated to a basic active ingredient may also be very low, in particular inferior to the minimal inhibiting concentration of fluoride anion $F^-$.

As an example, the inventors have found that when a solution containing 0.003% of benzalkonium chloride and a solution containing 0.0001% of fluoride anion $F^-$ each do not have a total spermicide activity according to the IPPF test, a solution containing 0.003% benzalkonium chloride and 0.001% of fluoride anion $F^-$ both together does satisfy the IPPF test. A synergistic effect is therefore observed.

TEST N· 3

This test consists in realizing a test identical to tests N· 1 and 2 above mentioned, but in presence of sodium borate, in order to complex ion $F^-$: the spermicidal effect of ion $F^-$ has totally disappeared, thus demonstrating that only ion $F^-$ is active or potentiator of the spermicidal effect.

TEST N· 4

Under the same conditions previously described (Tests N· 1 to 3), various perfluorinated benzalkonium chlorides were used as basic spermicidal compounds. It was thus shown that perfluorinated benzalkonium chlorides have a spermicide activity similar to the one of the mere benzalkonium chloride. Besides, this activity remains identical to itself under the conditions of test N· 3, in presence of sodium borate, which demonstrates that fluorine fixed on the benzine nucleus was not ionized.

Test N· 2 was also realized on perfluorinated benzalkonium chloride mixed with another chemical compound capable of emitting ion $F^-$. The potentiation of the spermicide activity of the perfluorinated benzalkonium chloride was also observed. This same test realized in presence of sodium borate (according to test N· 3) did induce a spermicide activity which is the one of perfluorinated benzalkonium chloride.

These two tests N· 3 and 4 show that the potentiation of the basic active ingredient only takes place in presence of fluoride anion $F^-$.

For manufacturing a spermicidal pharmaceutical product according to the invention, a solution with a given concentration in fluoride anion $F^-$ and, eventually, in basic active ingredient is realized and integrated in the excipient chosen according to the galenical form which is intended to be manufactured. In the case of the tablet, the basic active ingredient and the chemical compound capable of emitting ion $F^-$ are integrated to the excipient in the form of primary products.

COMPARATIVE TEST N· 5

This test in vitro was conducted on galenical preparations including benzalkonium chloride as basic active ingredient, by determining the MIC of this benzalkonium chloride after simulation in vitro of the actual conditions in vivo (extraction, solubilization . . . ).

This test conducted without activating ingredient induced the following results:

| Galenical form | MIC (% in weight) of benzalkonium chloride |
|---|---|
| ovule | 0.0063 |
| Cream | 0.0083 |
| Tampon | 0.0075 |
| Tablet | 0.0095 |
| Soluble waffle | 0.0080 |
| Gel | 0.0080 |

The percentages correspond to the proportions (in weight) of benzalkonium chloride in the solution used in vitro for the spermicidal test according to IPPF and obtained after simulation, the proportions being measured by titrating using a sample taken off from the solution.

TEST N· 6

The same conditions as during the comparative test N· 5 were used, but from galenical forms each originally containing 0.45% (in weight) of fluoride anion $F^-$.

The following results were obtained:

| Galenical form | MIC (% in weight) of benzalkonium chloride |
|---|---|
| ovule | 0.0023 |

| Galenical form | MIC (% in weight) of benzalkonium chloride |
|---|---|
| Cream | 0.0030 |
| Tampon | 0.0025 |
| Tablet | 0.0025 |
| Soluble waffle | 0.0017 |
| Gel | 0.0033 |

II) USE OF THE INVENTION FOR ANTISEPSIS, ANTIBIOTICS, ... AND IN PARTICULAR FOR FIGHTING AGAINST THE STD:

The preferred embodiments of the invention for its use, e.g. as antiseptic in dermatology are the following ones:

CREAMS AND MILKS:

| | |
|---|---|
| benzalkonium chloride | 1.20% |
| anion $F^-$ | 0.50% |
| (e.g. sodium fluoride) | |

Excipients: distilled or purified water, humectants, emulsifiers, stabilizers, antioxygens, antiseptics (to be included in variable proportions according to the viscosity and pH to be obtained).

OINTMENTS AND POMMADES:

| | |
|---|---|
| benzalkonium chloride | 1.20% |
| anion $F^-$ | 0.50% |
| (e.g. sodium fluoride) | |

Excipients: distilled or purified water, emulsifiers, excipients of the kind of the fatty compounds (vaseline, lanoleine, lanovaseline, stearovaseline), stabilizers, antioxygens, antiseptics (to be included in variable proportions according to the viscosity and pH to be obtained).

SYNTHETIC SOAPS:

| | |
|---|---|
| benzalkonium chloride | 2% |
| anion $F^-$ | 1% |
| (e.g. sodium fluoride) | |

Excipients: foaming and wetting products compatible with quaternary ammonia (e.g. amphoteric surfactant such as betaine or amino-betaine) emollients, stabilizers, antioxygens, antiseptics.

SOLUTIONS:

| | |
|---|---|
| benzalkonium chloride | 0.50% |
| anion $F^-$ | 0.25% |
| (e.g. sodium fluoride) | |

Excipients: distilled or purified water, ethanol, antioxygens, glycerine, sorbitol, antiseptics (to be included in variable proportions according to the pH to be obtained).

The preferred embodiments of the invention for its use, e.g. as local antibiotic in dermatology are the following ones:

SOLUTION:

| | |
|---|---|
| erythromycine base | 4% |
| anion $F^-$ | 0.5% |

Excipients: ethyl alcohol, propylene glycol, distilled water.

GEL:

| | |
|---|---|
| erythromycine base | 4% |
| anion $F^-$ | 0.5% |

Excipients: ethyl alcohol, hydroxypropylcellulose, distilled water, glycerine.

POMMADES:

| | |
|---|---|
| neomycin base | 0.35% |
| anion $F^-$ | 0.50% |
| or | |
| bacitracin | 50.000 IU % |
| anion $F^-$ | 0.50% |
| or | |
| oxytetracycline chlorhydrate | 3% |
| anion $F^-$ | 0.50% |
| or | |
| aureomycin chlorhydrate | 3% |
| anion $F^-$ | 0.50% |

Excipients: vaseline, vaseline oil, lanoline.

CREAMS:

| | |
|---|---|
| soframycin sulfate | 2.5% |
| anion $F^-$ | 0.50% |

Excipients: propylene glycol, polyoxyethyleneglycol, distilled water.

The preferred embodiments of the invention for its use, e.g. as local antibiotic in otorhinolaryngology are the following ones:

OPHTALMIC POMMADES:

| | |
|---|---|
| aureomycin | 1% |
| anion $F^-$ | 0.50% |
| or | |
| oxytetracycline | 0.50% |
| anion $F^-$ | 0.25% |

Excipients: vaseline, vaseline oil, lanoline

NASAL SOLUTIONS:

| | |
|---|---|
| soframycin sulfate | 1.25% |
| anion $F^-$ | 0.50% |

Excipients: distilled water, citric acid, sodium chloride.

For increasing the activity of the local antibiotherapeutical preparations, 0.10% of benzalkonium chloride may advantageously be added.

The preferred embodiments of the invention for its use, e.g. in gynecology and more particularly for fighting against the sexually transmissible diseases STD are those described under the item "USE OF THE INVENTION FOR LOCAL CONTRACEPTION" and under the denominations "OVULES", "CREAMS", "OINTMENTS AND POMMADES", "GELS", "TABLETS", "SYNTHETIC SOAPS" and "SOLUTIONS".

The methodology used in the tests conducted for those uses of the invention was as follows:

*for Neisseria gonorrhoea*

The used germs come from hospital isolations dilution range of the substances to be tested: Solvent: bidistilled sterile $H_2O$ Range with geometrical ratio of 2 Doses: from 2000 to 1.56 (and less) µgml 2 ml of each of the dilutions are mixed with 18 ml of solid preferable culture medium: gelose medium for isolation of gonococci (Institut Pasteur) enriched with G supplement:

| Formula: | Poulain serum | 165 ml |
|---|---|---|
| | yeast extract | 100 ml |
| | globular extract | 235 ml |
| | glucose | 0.65 ml |

-continued

| | |
|---|---|
| distilled H₂O to make up for | 500 ml |

Culture medium of the gonococci: 2000 ml of Pasteur medium+500 ml of G supplement.

Those culture medium associated to the dilutions of the active substances form the investigation means of the bactericide activity. The final concentrations of the substances are about from 800 to 0.156 µg/ml in the Petri dishes. The used suspensions (dilution in physiological water of a 24 hours-culture in nutritive liquid-broth medium) are placed in wells hollowed in a synthetic base under laminar-flow hood. In each of the prepared wells, a strain (multiple seeder) is studied. Each studied dish is examined after 24 and 48 hours of culture (stove at 37° C.).

Determination of the MIC: the gonococci strains are spreaded on plates (dilution on plate) some of them being prepared as comparative and control strains without substance to be tested.

5 µof 10 formative colonies/ml are deposited on the gelose plates completed or not with the substances to be tested (18 hours culture of gonococci suspended in a Sorensen solution).

A 48 h incubation at 36° C. is carried out, then the growth or the lack of growth of the gonococci is observed on the plates.

*for Candida albicans:*

The methodology is substantially the same as for *Neisseria gonorrhoeae*, but with the following differences:

Dilution range in bidistilled sterile water from 2000 to 1.56 µg/ml.

0.5 ml of each dilution is added to 4.5 ml of liquid Roiron medium.

The tubes are seeded with cultures of Candida (24 hours/Roiron medium) or with the comparative strain (Roiron medium). The incubation of the tubes is conducted in stove at 37° C. during 24 and 48 hours. At t=24 hours and t=48 hours, observation of a drop between slide and cover-glass under microscope.

Expression of the results by accounting the yeasts and determination of the fungicide MIC. On comparative tubes, determination of the percentage in resistants.

for *Trichomonas vaginalis:*
Same methodology as for *Candida albicans.* for Chlamydia:

Inoculum: it is constituted by the host-cells of chlamydia or Mac Coy cells. They are preserved at
80° C. The cellular concentration is from 2 to 2.5×10 cells/ml for the tests. The cellular layer is prepared in a complete culture medium.

The substances to be tested are diluted with an increasing range which geometrical ratio is 2 in bidistilled sterile water.

The used method is the one of Professors F. CATALAN, P. SEDNAOUI, A. MILOVANOVIC and al., A. FOURNIER INSTITUTE, Paris.

1 ml of dilution of the substances to be tested is mixed with 1 ml of cellular suspension (Mac Coy cells). then incubated 1 hour and 24 hours at 37° C. in stove. 0.2 ml of this admixture is then placed in the plates of the wells. The plates are centrifugated (1 hour at 2000 rpm) and incubated 1 hour at 37° C. The culture medium is then replaced with 0.2 ml of new medium containing 0.5 mg1 of cycloheximide and the plates are then incubated 48 hours at 37° C. The cellular layer is then fixed with methanol and overall couloured with a monoclonal antibody and conjugate with FITC (fluorescein isothiocyanate). Then the inclusions present in the Mac Coy cells are observed with an inversed epifluorescence microscope.

Therefore, the toxicity of the substances to be tested was first tested, and was taken into account for totally respecting the integrity of the host-cell.

for *Pseudominas aeruginosa:*

Preparation of a dense solution with two strains.

Suspension in isotonic solution of NaCl (0.85% weight).

Checking that the suspensions include the same number of bacteria: regular techniques in gelose medium by grooved seeding (1 µl ansa) of the successive dilutions of the original dense solutions (geometrical ratio 10). Incubation 18 hours at 37° C.

Preparation of the dilutions of the substances to be tested in solution in bidistilled sterile water. Range of dilution with geometrical ratio of 2 (e.g. from 2000 to 0.015 µg/ml).

Admixture of the *Pseudominas aeruginosa* bacterial suspension (same origin as the AFNOR standards), with a constant concentration ($=4\times10^7$ bacteria/ml) and with the dilution of the substances in a decreasing order (2000 to 0.015 µg/ml).

Incubation or contact time: 1 hour, 24 hours and 48 hours in stove at 37° C.

| STRAINS | Minimal inhibiting concentration (MIC) Nonoxynol 9 alone |
|---|---|
| Treponema | 75 mg/l |
| Pseudomonas Aeruginosa | 50 mg/l |
| Staphylococcus Aureus | 4 mg/l |
| Streptococcus | 20 mg/l |

TEST N° 8

The same test as precedently, conducted in presence of fluoride anion F⁻ gave the following results:

| STRAINS | Minimal inhibiting concentration (MIC) Benzalkonium fluoride + F⁻ 1 microgram/ml |
|---|---|
| Gonococcus | 0.60 mg/l |
| Treponema | 56 mg/l |
| Trichomonas | 0.9 mg/l |
| Candidas Albicans | 35 mg/l |
| Chlamydia | 85 mg/l |
| Gardnerella | 41 mg/l |
| Ducrey's Bacillus | 62 mg/l |
| Streptococcus | 9 mg/l |
| Pseudomonas Aeruginosa | 18 mg/l |
| Staphylococcus Aureus | 1.1 mg/l |

The tests were doubled for each dilution of substance.

Observation of the number of survivors recorded with regard to the average number of the comparative strains cultured simultaneously with the tests.

Observation after 1 hour, 24 hours and 48 hours.

for Treponema, Gardnerella, Ducrey's Bacillas, Streptococci and *Staphylococcus aureus*

The methodology used is the one described by Professors F. CATALAN, P. SEDNAOUI, A. MILOVANOVIC and al., A. FOURNIER INSTITUTE.

COMPARATIVE TEST N° 7

With benzalkonium chloride alone and nonoxynol 9 alone, the following results were obtained:

| STRAINS | Minimal inhibiting concentration (MIC) |
|---|---|
| | Benzalkonium fluoride alone |
| Gonococcus | 1.15 mg/l |
| Treponema | 70 mg/l |
| Trichomonas | 1.3 mg/l |
| *Candidas Albicans* | 50 mg/l |
| Chlamydia | 100 mg/l |
| Gardnerella | 50 mg/l |
| *Ducrey's Bacillus* | 75 mg/l |
| Streptococcus | 15 mg/l |
| *Pseudomonas Aeruginosa* | 31.25 mg/l |
| *Staphylococcus Aureus* | 1.56 mg/l |
| | Nonoxynol 9 + $F^-$ 1 microgram/ml |
| Treponema | 60 mg/l |
| *Pseudomonas Aeruginosa* | 35 mg/l |
| *Staphylococcus Aureus* | 2.5 mg/l |
| Streptococcus | 15 mg/l |

COMPARATIVE TEST N° 9

This test was conducted with a substance including benzalkonium chloride without activating ingredient but in presence of serous proteins. It gave the following results:

| STRAINS | CONCENTRATIONS IN SEROUS PROTEINS | Minimal inhibiting concentration (MIC) Benzalkonium chloride alone |
|---|---|---|
| Streptococcus Faecalis | 0 | 15 mg/ml |
| | 30 mg/ml | 15 mg/ml |
| | 60 mg/ml | 16 mg/ml |
| | 90 mg/ml | 68 mg/ml |
| Neisseria Gonorrhoeae | 0 | 1.5 mg/ml |
| | 30 mg/ml | 1.5 mg/ml |
| | 60 mg/ml | 1.5 mg/ml |
| | 90 mg/ml | 9 mg/ml |

This test shows the known unfavourable effect of the serous proteins upon the efficiency of benzalkonium chloride.

TEST N° 10

This test was conducted identically with test N° 9, but in presence of fluoride anion $F^-$ in the composition. The following results were obtained.

| STRAINS | CONCENTRATIONS IN SEROUS PROTEINS | Minimal inhibiting concentration (MIC) Benzalkonium chloride + $F^-$ 1 microgram/ml |
|---|---|---|
| Streptococcus Faecalis | 0 | 9 mg/ml |
| | 30 mg/ml | 9 mg/ml |
| | 60 mg/ml | 9 mg/ml |
| | 90 mg/ml | 21 mg/ml |
| Neisseria Gonorrhoeae | 0 | 0.6 mg/ml |
| | 30 mg/ml | 0.6 mg/ml |
| | 60 mg/ml | 0.6 mg/ml |
| | 90 mg/ml | 1.2 mg/ml |

This test shows that fluoride anion $F^-$ advantageously decreases the unfavourable effect of the serous proteins.

COMPARATIVE TEST N° 11

This test was conducted on galenical forms in vitro (similarly to tests N° 5 et 6), with products containing benzalkonium chloride as active ingredient and free of activating ingredient.

The following results were obtained:

| STRAINS | GALENIC FORM | Minimal inhibiting Concentration (MIC) Benzalkonium chloride alone |
|---|---|---|
| Gonococcus | ovule | 23.65 mg/l |
| | tablet | 15.62 mg/l |
| Trichomonas | ovule | 11.80 mg/l |
| | tablet | 15.60 mg/l |

The concentrations are those present in the liquid obtained after simulation, used for the test.

TEST N° 12

This test was conducted in the same conditions as the comparative test N° 11 from products containing 0.5% (in weight) of fluoride anion $F^-$.

The following results were obtained

| STRAINS | GALENIC FORM | Minimal inhibiting Concentration (MIC) Benzalkonium chloride + 0.5% $F^-$ |
|---|---|---|
| Gonococcus | ovule | 5 mg/l |
| | tablet | 3 mg/l |
| Trichomonas | ovule | 5 mg/l |
| | tablet | 3 mg/l |

III) USE OF THE INVENTION IN THE FIELD OF DISINFECTION:

This field relates to the treatment of floors, surfaces, instruments . . . with contact bactericidal products.

The preferred embodiments of the invention for this use are as follows:

| UTILIZATIONS | Benzalkonium Chloride | Anion F⁻ | Excipients |
|---|---|---|---|
| Hands Epidermis | 0.1% | 0.25% | purified water or alcohol to make up for 100% |
| Instruments to be sterilized to be disinfected | 1.0% | 0.50% | purified water to make up for 100% |
| Textiles | 0.05% | 0.025% | purified water to make up for 100% |
| Instruments (e.g. thermometer) | 1.0% | 0.50% | Ethanol 10% purified water to make up for 100% |
| Cleaning of surfaces (rooms, floor . . . ) | 0.1% | 0.25% | purified water to make up for 100% |

The tests were conducted according to the standard AFNOR NFT 72–150, March 1981, with benzalkonium chloride, then with nonoxynol 9 as active ingredient.

The neutralizer used was as follows: 3% Tween 80 (V/V) and 0.3% lecithin (MV). The pH of the medium was 7.2.

COMPARATIVE TEST TEST N⁻13

This test was conducted without activating ingredient:

| STRAINS | Minimal inhibiting Concentration (MIC) |
|---|---|
| | Benzalkonium chloride alone |
| Pseudomonas aeruginosa CNCM A 22 | 31.25 mg/l |
| Escherichia coli CNCM 54 127 | 6.57 mg/l |
| Staphylococcus Aureus Oxford origin CNCM 53 154 | 1.56 mg/l |
| Streptococcus faecalis CNCM 5 855 | 4 mg/l |
| Mycobacterium smegmatis CNCM 7 326 | 30 mg/l |
| | Nonoxynol 9 alone |
| Pseudomonas aeruginosa CNCM A 22 | 50 mg/l |
| Escherichia coli CNCM 54 127 | 8 mg/l |
| Staphylococcus Aureus Oxford origin CNCM 53 154 | 4 mg/l |
| Streptococcus faecalis CNCM 5 855 | 7 mg/l |
| Mycobacterium smegmatis CNCM 7 326 | 65 mg/l |

TEST N⁻ 14

This test is identical to the previous one but in present of fluoride anion F⁻ as activating ingredient.

| STRAINS | Minimal inhibiting Concentration (MIC) |
|---|---|
| | Benzalkonium chloride + F⁻ 1 microgram/ml |
| Pseudomonas aeruginosa CNCM A 22 | 18 mg/l |
| Escherichia coli CNCM 54 127 | 3 mg/l |
| Staphylococcus Aureus Oxford origin CNCM 53 154 | 1.1 mg/l |
| Streptococcus faecalis CNCM 5 855 | 3.6 mg/l |
| Mycobacterium smegmatis CNCM 7 326 | 26 mg/l |
| | Nonoxynol 9 + F⁻ 1 microgram/ml |
| Pseudomonas aeruginosa CNCM A 22 | 35 mg/l |
| Escherichia coli CNCM 54 127 | 6.5 mg/l |
| Staphylococcus Aureus Oxford origin CNCM 53 154 | 2.5 mg/l |
| Streptococcus faecalis CNCM 5 855 | 5.5 mg/l |
| Mycobacterium smegmatis CNCM 7 326 | 50 mg/l |

IV) USE OF THE INVENTION IN COSMETOLOGY:

The preferred embodiments of the invention in cosmetology are described hereinafter:

The following galenical forms may be presented in cosmetology: creams, milks, pommades, solutions, foaming bath, synthetic soaps, shampoos, intimate lotions, disinfecting lotions.

The formula of the excipients are the same as for the pharmaceutical preparations but the concentrations in benzalkonium chloride and anion F⁻ are different. Those concentrations are preferably as follows for all the products: 0.2% benzalkonium chloride and 0.1% fluoride anion F⁻.

Chemical or naturally originated active ingredients may also enter into these formulae with concentrations and doses which are allowed in cosmetology.

The creams and milks may be in continuous aqueous phase (oil/water or water/oil emulsion) or pasty when warm, self diluting in water.

The various excipients referred to as examples correspond in a non-restrictive and indicative way to the following products:

Humectants: glycerol, propylene glycol, diethylene glycol, glycol, sorbitol, polyoxyethylene glycol.

Emulsifiers: sodium stearate, beeswax, sorbitolester, polyoxyethylene glycol ester, fatty alcohol, triethanolamine lanoline, tween, glycol stearate and polyglycols.

Stabilizers: glycol stearate, cetylic alginate alcohol, pectin, gum, fatty esters of polyols, soluble cellulose esters.

Antioxygens: tartaric acid, citric and ascorbic acid.

Antiseptic: boric acid, benzoic acid, parabenzoic acid, and their methylic or propylic esters, soded or not.

PH: all these formulas are particularly efficient with pH comprised between 4.5 and 6.5. For obtaining such a range, citric acid is mainly used.

V) Use of the invention for inhibition or destruction of viruses or retroviruses.

The preferred embodiments of the invention for inhibiting viruses or retroviruses are described hereinafter:

The following forms may be used: cream, milk, ointment, pomade, gel or solution.

The formula of the excipients are the same as previously presented. The benzalkonium chloride is preferably present in an amount of from 0.1 to 2%, while the fluoride anions are preferably present in an amount of from 0.025% to 0.50%. The anions may be present in form of FNa.

Test No. 15

All the doses of the antiseptics used are, obviously, less than the threshold of cytotoxicity recorded above. From the mixtures containing an equal volume of vital suspension and antiseptic, 1 ml is withdrawn at 30, 60, 120 and 180 minutes. The samples are then deposited on SEPHADEX columns, after which they are centrifuged. In parallel, a control viral suspension without antiseptic is processed under the same conditions.

The results are given in the following tables:

BKC: Benzalkonium chloride
BKF: Benzalkonium fluoride
LiF: Lithium fluoride

| Study of threshold of cytoxicity (LDO) | | |
| --- | --- | --- |
| Antiseptic | Before filtration | After filtration |
| BKC | 0.05% | 0.01% |
| BKC + LiF | 0.05% | 0.01% |
| BKF | 0.01% | 0.005% |
| BKF + LiF | 0.01% | 0.005% |

| Capacity of the cells to develop the viral infection | | | | |
| --- | --- | --- | --- | --- |
| Titre of the viral suspensions (PFU/ml) | | | | |
| Control virus | BKC + virus | BKC + LiF§ + virus | BKF + virus | *BKF + LiF§ + virus |
| $10^{7.94}$ | $10^{7.84}$ | $10^{7.84}$ | $10^{6.84}$ | $10^{6.04}$ |

PFU = plaqueforming unit (PFU/ml)

Virucidal activity of the antiseptics with respect to poliomyelitis virus after gel filtration, in terms of the contact time

| Antiseptic | Final concentration (in mg/l) | Viral titre expressed in PFU/ml virus/antiseptic contact time | | | |
| --- | --- | --- | --- | --- | --- |
| | | 30 min | 60 min | 120 min | 180 min |
| Benzalkonium chloride | 200 | $10^{1.74}$ | $10^{1.74}$ | $10^{1.74}$ | $10^{1.64}$ |
| | 100 | 0 | 0 | 0 | 0 |
| | 50 | $10^{1.74}$ | $10^{1.74}$ | $10^{1.64}$ | 0 |
| | 20 | $10^{1.84}$ | $10^{1.84}$ | $10^{1.74}$ | 0 |
| | 10 | $10^{4.84}$ | $10^{3.84}$ | $10^{3.84}$ | ≈0 |
| Benzalkonium chloride + Lithium fluoride (1 mg/l) | 200 | $10^{1.84}$ | $10^{1.84}$ | $10^{1.74}$ | $10^{1.74}$ |
| | 100 | 0 | 0 | 0 | 0 |
| | 50 | $10^{1.84}$ | $10^{1.84}$ | $10^{1.84}$ | 0 |
| | 20 | $10^{1.74}$ | $10^{1.84}$ | $10^{1.64}$ | 0 |
| | 10 | $10^{3.84}$ | $10^{3.84}$ | $10^{3}$ | 0 |
| Benzalkonium fluoride | 200 | $10^{1.74}$ | $10^{1.74}$ | $10^{1.64}$ | $10^{1.84}$ |
| | 100 | 0 | 0 | 0 | 0 |
| | 50 | $10^{1.34}$ | $10^{1.34}$ | 0 | 0 |
| | 20 | $10^{1.64}$ | $10^{1.64}$ | $10^{1.64}$ | 0 |
| | 10 | $10^{2.54}$ | $10^{2.54}$ | $10^{2.34}$ | $10^{2.34}$ |
| Benzalkonium fluoride + Lithium fluoride (1 mg/l) | 200 | $10^{1.74}$ | $10^{1.74}$ | $10^{1.84}$ | $10^{1.84}$ |
| | 100 | 0 | 0 | 0 | 0 |
| | 50 | $10^{1.3}$ | $10^{1.3}$ | 0 | 0 |
| | 20 | $10^{1.84}$ | $10^{1.74}$ | $10^{1.34}$ | 0 |
| | 10 | $10^{3.84}$ | $10^{3.84}$ | $10^{3}$ | $10^{8.54}$ |

Test No. 16

Virucidal activity according to the AFNOR Standard:

The virucidal activity of benzalkonium fluoride was determined following AFNOR Standard T72-180. The following results were obtained:

| | Inhibitory concentration (% by weight) | Cell Toxicity |
| --- | --- | --- |
| 1/ On type 2 herpes simplex virus: | | |
| Benzalkonium chloride | 0.01% | 0.05% |
| Benzalkonium fluoride | 0.0075% | 0.08% |
| 2) On cytomegalo virus: | | |
| Benzalkonium chloride | 0.01% | 0.05% |
| Benzalkonium fluoride | 0.0075% | 0.05% |

What is claimed is:

1. An antiviral or antiretroviral composition for inhibiting or destroying herpes II virus in a mammalian host, which composition comprises a surfactant selected from the group consisting of quaternary ammonium compounds and nonoxynyl, a fluorinated compound which is a metallic derivative of fluorine, which compound is capable of releasing from 0.025% to 0.50% by weight of fluoride anions, and an excipient.

2. An antiviral or antiretroviral composition for inhibiting or destroying HIV virus in a mammalian host, which composition comprises a surfactant selected from the group consisting of quaternary ammonium compounds and nonoxynyl, a fluorinated compound which is a metallic derivative of fluorine, which compound is capable of releasing from 0.025% to 0.50% by weight of fluoride anions, and an excipient.

3. An antiviral or antiretroviral composition for inhibiting or destroying virus selected from the group consisting of HIV virus-1 and HIV virus-2 in a mammalian host, which composition comprises a surfactant selected from the group consisting of quaternary ammonium compounds and nonoxynyl, a fluorinated compound which is a metallic derivative of fluorine, which compound is capable of releasing from 0,025% to 0.50% by weight of fluoride anions, and an excipient.

4. An antiviral or antiretroviral composition for inhibiting or destroying virus selected from the group consisting of parvo virus and distemper virus in a mammalian host, which composition comprises a surfactant selected from the group consisting of quaternary ammonium compounds and nonoxynyl, a fluorinated compound which is a metallic derivative of fluorine, which compound is capable of releasing from 0.025% to 0.50% by weight of fluoride anions, and an excipient.

5. A method for inhibiting or destroying herpes II virus in a mammalian host which comprises contacting said virus with the composition as claimed in claim 1.

6. A method for inhibiting or destroying HIV virus in a mammalian host which comprises contacting said virus with the composition as claimed in claim 2.

7. A method for inhibiting or destroying virus selected from the group consisting of HIV-1 virus and HIV-2 virus in a mammalian host which comprises contacting said virus with the composition as claimed in claim 3.

8. A method for inhibiting or destroying virus selected from the group consisting of parvo virus and distemper virus in a mammalian host which comprises contacting said virus with the composition as claimed in claim 4.

9. A method for inhibiting or destroying in a mammalian host a virus selected from the group consisting of herpes II, HIV-1, HIV-2, parvo and distemper, which method comprises administering to said host an effective amount of a composition which comprises

- a surfactant selected from the group consisting of quaternary ammonium compounds and nonoxynyl,
- a fluorinated compound which is a metallic derivative of fluorine, which compound is capable of releasing from 0.025% to 0.50% by weight of fluoride anions, and an excipient.

10. A method as defined in claim 9, which comprises effecting said administration by oral, intravenous, subcutaneous injection, or topical means.

* * * * *